United States Patent [19]
Lisiecki

[11] Patent Number: 6,083,156
[45] Date of Patent: Jul. 4, 2000

[54] PORTABLE INTEGRATED PHYSIOLOGICAL MONITORING SYSTEM

[75] Inventor: Ronald S. Lisiecki, 815 E. Yale Ave. #C, Salt Lake City, Utah 84105-1330

[73] Assignee: Ronald S. Lisiecki, Salt Lake City, Utah

[21] Appl. No.: 09/192,714

[22] Filed: Nov. 16, 1998

[51] Int. Cl.[7] .................................................. A61B 5/0205
[52] U.S. Cl. ........................................................... 600/301
[58] Field of Search ..................................... 600/300, 301, 600/503, 509, 534, 544

[56] References Cited

U.S. PATENT DOCUMENTS

| 4,686,998 | 8/1987 | Robbins | 128/670 |
|---|---|---|---|
| 4,827,943 | 5/1989 | Bornn | 128/668 |
| 4,860,759 | 8/1989 | Kahn | 128/668 |
| 4,889,131 | 12/1989 | Salem | 128/671 |
| 4,974,607 | 12/1990 | Miwa | 128/904 |
| 5,012,411 | 4/1991 | Policastro | 364/413.06 |
| 5,238,001 | 8/1993 | Gallant | 128/700 |
| 5,257,627 | 11/1993 | Rapoport | 128/661.07 |
| 5,263,491 | 11/1993 | Thornton | 128/774 |
| 5,275,159 | 1/1994 | Griebel | 128/633 |
| 5,339,821 | 8/1994 | Fujimoto | 128/700 |
| 5,375,604 | 12/1994 | Kelly | 128/671 |
| 5,417,222 | 5/1995 | Dempsey | 128/696 |

Primary Examiner—Max Hindenburg
Attorney, Agent, or Firm—Garron M. Hobson

[57] ABSTRACT

A portable, integrated physiological monitoring system is described for use in clinical outpatient environments. This systems consists of a plethora of sensors and auxiliary devices, an electronics unit (100) that interfaces to the sensors and devices, and a portable personal computer (102). Electrodes (106) are provided to acquisition electrocardiographic, electroencephalographic, and neuromuscular signals. Electrodes (108) are provided to stimulate neural and muscular tissue. A finger pulse oximeter (110), an M-mode ultrasonic transducer (112), an airflow sensor (114), a temperature probe (120), a patient event switch (116), and an electronic stethoscope (118) are provided. A portable personal computer (102) interfaces to the electronics unit (100) via a standard parallel printer port interface (258) to allow communication of commands and information to/from the electronics unit (100). Control and display of the information gathered from the electronics unit (100) is accomplished via an application program executing on the portable personal computer (102). Sharing of common data acquisition hardware along with preliminary processing of information gathered is accomplished within the electronics unit (100). The entire system is battery operated and portable. This system, because of its architecture, offers significant cost advantages as well as unique modes of operation that cannot be achieved from the individual physiological parameter measurement devices alone. The system allows for the integration of acquisitioned information from the sensors into a patient's database stored on the portable personal computer.

20 Claims, 2 Drawing Sheets

PORTABLE INTEGRATED PHYSIOLOGICAL MONITORING SYSTEM

BACKGROUND

1. Field of Invention

This invention relates to portable systems capable of acquisitioning, displaying, and recording physiological information obtained from a human subject.

2. Description of Prior Art

Medical clinicians often need to assess physiological information from a human subject in order to diagnose or monitor disease states. In clinical outpatient environments, the scope of this information widely ranges from cardiac information (i.e. ElectroCardioGrams [ECGs]) to pulmonary information (i.e. Pulmonary Function Tests [PFTs], pulse oximetry [$S_aO_2$]) to neurologic information (i.e. ElectroEncephaloGrams [EEGs], nerve conduction studies).

Current devices used to assess such physiological information are commonly available to clinicians and exist in numerous configurations. Typically, most of these configurations consist of a single device that assesses a single or related group of physiological parameters. This device is usually dedicated only to the acquisition of physiological information for one organ system of the human subject that is being tested. Typical examples of these devices include the electrocardiogram and the pulmonary function test. A few devices acquisition information from more than one organ system such as the PROPAQ System (U.S. Pat. No. 5,568,814 [1996]) manufactured by PROTOCOL Systems, Inc. which is capable of recording electrocardiograms, oxygen saturation, and blood pressure. These multiorgan, physiological monitoring systems are useful in portable/ambulatory situations where temporary monitoring of multiple physiologic parameters is required but, such systems lack utility in clinical outpatient environments where more parameters may be required to be assessed and where these parameters need to be integrated into the patients medical record.

Current devices are typically electrically powered from commercial power found in most office environments. Some devices are battery powered for portable operation such as the PROPAQ device mentioned above. The utility of portability of such devices is attained when the device is battery powered and many situations in a clinical outpatient environment benefit from this portability by having equipment that can be easily moved from one setting to another. An example of such utility is seen in today's portable finger pulse oximeters.

Current devices are limited in their ability to transmit their acquired information to locations where that information could be best utilized or stored. The predominant method of data storage is the hand-copying of the acquired information from the device to the patient's medical record (e.g. a blood pressure measurement or a finger oximeter measurement). Alternatively, the device may print either a strip or a page of paper which is retrieved and placed in the medical record. Both of these methods fail to "integrate" the information into the patient's medical record in a manner that is timely, that maximizes its utility there, and that minimizes loses of such acquired information.

The majority of devices used to collect physiological information from a human subject utilize electrical circuitry that must convert a transduced signal into a digital value (i.e. analog-to-digital conversion) which is then usually manipulated by a digital processing element (i.e. microprocessor,or digital signal processor) into either displayable information, and/or a transmittable/storable element. Since the majority of devices utilize this method, it would seem reasonable if these devices could share their common conversion and manipulation elements by combining them into a common unit. This would offer significant cost advantages in the common unit as compared to the individual devices since redundant electrical hardware is shared among the signals to be transduced and manipulated.

Furthermore, alphanumeric as well as graphical information is commonly generated by these devices and is typically displayed on the front panel of such devices or is printed on paper medium. It would also be reasonable to share a common display device in a unit that would contain functions combining various measurement parameters so that a cost advantage could be obtained by sharing this common display device. This concept of sharing of the display device could also be extended to the sharing of a common printing device, again, achieving further cost advantages.

Additionally, certain medical conditions could be diagnosed in the clinical outpatient environment if multiple and/or continuous monitoring of certain physiological parameters could be performed. Examples of these conditions include sleep apnea, dysrhythmias, and certain neurological/psychiatric conditions. It would be advantageous to be able to monitor and record these parameters within the clinical outpatient environment, and diagnose/monitor these medical conditions in this environment rather than having to send the subject to specialized centers needed to diagnose/monitor these conditions. Having these capabilities within the clinical outpatient environment could offer expense savings to our healthcare system.

As more and more medical information is collected on a particular human subject over the course of his/her medical history, the need to centrally collect this information, organize it, store it, and transmit it to other locations becomes a more difficult task. Currently, in the clinical outpatient environment at least, these tasks are manually performed. There is a paucity of systems that efficiently organize and store such information. A need exists for a system that can accomplish the above tasks that utilizes a cost effective system.

Several types of monitoring systems that acquisition multiple physiologic parameters are currently employed within inpatient as well as outpatient clinical environments. Many of these, such as in U.S. Pat. No. 4,860,759 (1989), are intended only to continuously monitor and display certain groups of physiological parameters. Others, such as U.S. Pat. Nos. 5,263,491 (1993), 5,275,159 (1994), 5,238,001 (1993), and 5,339,821 (1994) continuously monitor and log certain groups of physiological parameters for future playback and analysis, but, do not display the information while it is being acquisitioned. Still, other systems such as described in U.S. Pat. Nos. 4,686,998 (1987), 4,827,943 (1989), 5,012,411 (1991), 4,974,607 (1990), 4,889,131 (1989), and 5,257,627 (1993) continuously monitor certain groups of physiological parameters and transmit the information to remote sites for decision making. None of the above systems describe a system to acquisition selected physiological parameters in a clinical outpatient environment and display this information on a viewing device, as well as incorporate the information into the medical record, and, interpret and store this information at the collection site.

Other physiological monitoring systems described in U.S. Pat. Nos. 5,375,604 (1994) and 5,417,222 (1995) are either portable, multichannel systems for monitoring only (i.e. not intended to permanently record the data into a human subject's medical record) (the former patent) or bedside/intensive care type units with nonportable beside sensors (the latter patent). Both of these devices are also intended to transmit information to a central station for analysis and logging of this information at this location, but not at the bedside.

A few other relatively new systems (of particular interest is the "NAS" system from BCI International; no patent found at this time) are ambulatory monitoring systems with a limited number of physiological parameters that can be monitored and whose parameters can only be viewed statically (i.e. the device does not provide continuous monitoring of the physiologic variable of interest). These devices utilize a personal computer to acquisition and display static parameters only. Integration of the information into the patient's medical record is not a capability of these types of systems.

Technological advances in personal computers, especially portable personal computers, now allow many systems access to processing capabilities not available in the past. Portable personal computers now have ample processing power to allow them to control external systems in a real-time fashion. These computers also allow a system to utilize their display and keyboard for very sophisticated user interaction as well as information displays. Furthermore, these computers offer very large temporary, as well as long-term storage capabilities, that allow for management of large databases of information. These systems also allow for simplified communication of information to/from remote computing facilities. Finally, these portable computers are battery powered and allow for remote processing/control of an application where commercial power is not available. The numerous capabilities of personal portable computers present a very cost effective method of controlling and interacting with external systems that has otherwise not been available in the past.

Although many patient physiological monitoring systems currently exist, most of these are not appropriate for the measurement and management of physiological parameters of human subjects in the clinical outpatient environment. This environment demands the ability to monitor more physiological parameters than current systems offer within one system. The acquisition of these parameters from human subjects needs to be integrated into the patient's medical record in a timely, efficient, and reliable manner. The acquisition process should have the capability of being performed without the use of commercial power and the equipment used should be easily portable between various environments. Because the various subsystems used to acquisition physiological parameters utilize similar electrical components, a system incorporating these various subsystems should take advantage of the sharing of these components in an effort to minimize the cost of the overall system. The physiological monitoring system described in this document incorporates the above concepts into an apparatus for monitoring physiological parameters that has very high utility and low cost in a clinical outpatient environment.

OVERVIEW OF THE INVENTION: OBJECTS AND ADVANTAGES

A portable, integrated physiological monitoring system is described for principal use in clinical outpatient environments. This physiological monitoring system consists of three principal elements: a) a plethora of physiological sensors and auxiliary devices, b) a chassis of electronic components (electronics unit) that acquisitions information from the sensors and communicates this information to a portable personal computer, and c) a portable personal computer.

In the current embodiment of this physiological monitoring system, the plethora of sensors currently consists of a) electrodes for the acquisition of electrocardiographic, electroencephalographic and neuromuscular signals, b) electrodes to stimulate neural and muscular tissue, c) a finger pulse oximeter, d) an M-mode ultrasonic transducer, e) an airflow sensor, f) a handheld patient event switch, g) an electronic stethoscope, h) a temperature probe, and i) a pair of stereo headphones. It is envisioned that other sensors could easily be adapted to this system for acquisition of their respective signals/data.

The electronics unit consists of circuits that interface to the various external sensors, a rechargeable battery with charge status and charge control circuitry, a common analog-to-digital converter with a multiplexer, a digital signal processor to process the various streams of data coming from the sensors, memories to hold temporary data as well as permanent control instructions for the processors, a display/input/output microcontroller, a front panel status display, and an interface to the portable personal computer as well as to an external printer.

The portable personal computer resides on top of the electronics unit and interfaces to the unit via the parallel printer port of the portable personal computer. Commands from this portable personal computer are sent to the electronics unit via the parallel printer port interface to initiate and control acquisition of information from the sensors. Information collected from the electronics unit can be sent to the portable personal computer via the parallel printer port interface. The user interacts and controls the overall system operation from the keyboard and display of the portable personal computer. Information collected from the sensors can be displayed on the display of the portable personal computer in various formats. Real-time monitoring of continuous sensor information is possible. The hard disk drive of the personal computer can be utilized for long-term storage of acquisitioned information as well as for access and integration of information with the patient databases stored there. Communication with peripheral information systems may be accomplished through various standard communication pathways available on most portable personal computers. An external printer attached to the electronics unit allows for the ability of the system to print information from the portable personal computer while also being able to utilize the parallel printer port interface for control purposes.

Several objects and advantages of the present physiological monitoring systems are:

(a) to provide a plethora of physiological sensors that are useful to the medical clinician in a clinical outpatient environment;

(b) to share electronic elements (analog-to-digital converters and digital signal processors) that are common to the processing of information from the various attached sensors in a means that is conducive to the overall cost reduction of the device;

(c) to utilize the various processing, display and user interface capabilities of the portable personal computer to control the operations of the device thereby minimizing components that would have had to be incorporated into the electronics of the device in order to effect the same capabilities;

(d) to provide for the ability to monitor and display information continuously from sensors that provide real-time, continuous information;
(e) to provide a portable, battery powered device, that is capable of being easily transported to various locations;
(f) to provide a very low cost, common interface (i.e. the parallel printer port), between the device's electronics unit and the portable personal computer, for communication of commands and information between these devices;
(g) to provide for the integration of acquisitioned information from the device's sensors with the patients medical records stored within the personal computer or stored in a remote facility;
(h) to provide for the ability to acquisition multiple streams of continuous information from various sensors simultaneously in order to monitor/diagnose certain disease states;
(i) to provide greater access to the monitoring of physiological parameters for healthcare providers that may not be able to acquire individual devices capable of monitoring these parameters due to their higher costs;

Further objects will demonstrated from a consideration of the ensuing description and drawings.

DRAWING FIGURES

Figure 1:
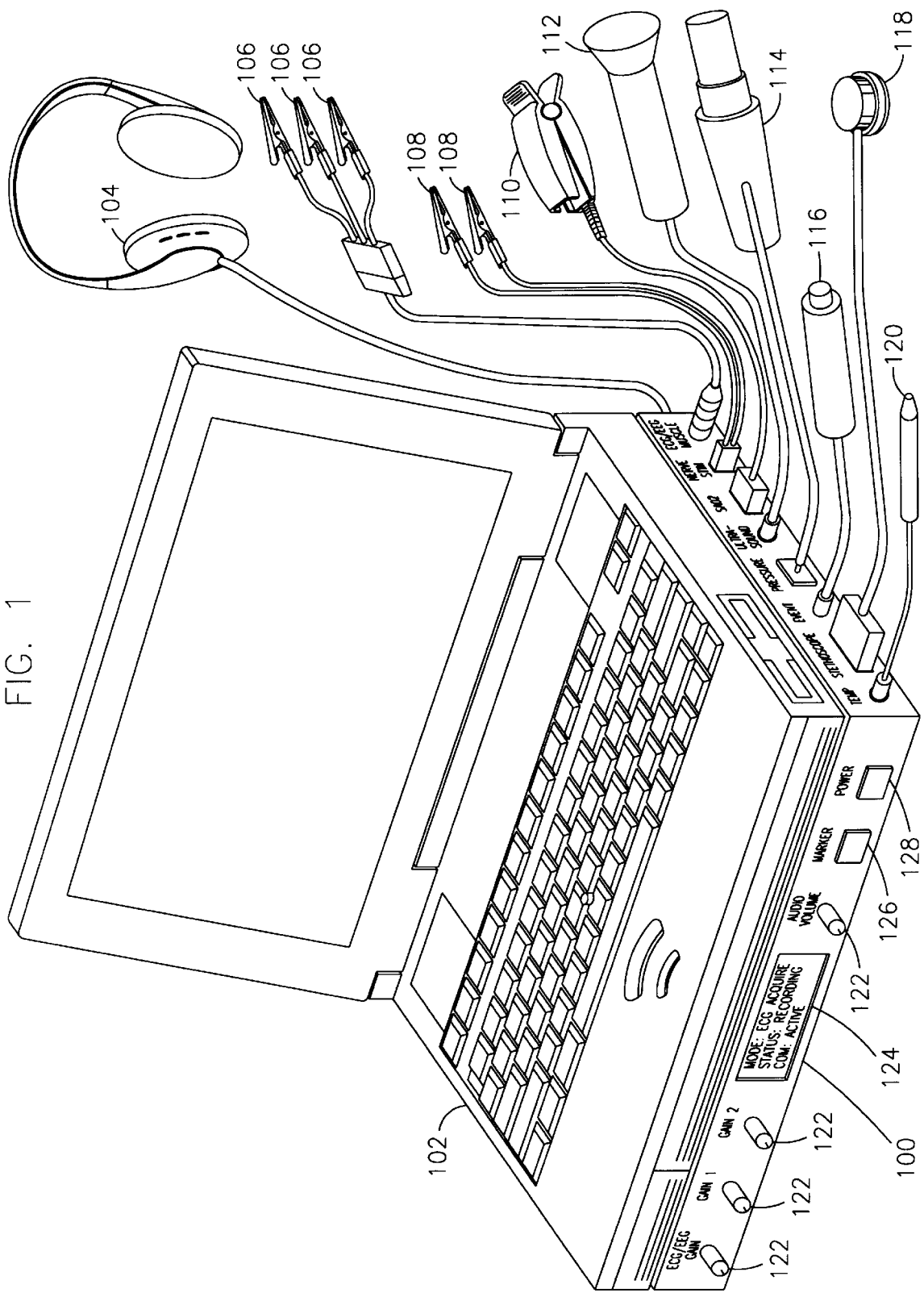
FIG. 1 shows a perspective view of the entire physiological monitoring system described in this patent which includes the sensors, the electronics unit, and the portable personal computer.

Reference Numerals in Drawings
100 electronics unit
102 portable personal computer
104 stereo headphones
106 alligator clips for ECG/EEG/Muscle electrodes
108 alligator clips for nerve/muscle stimulator electrodes
110 finger pulse oximeter
112 M-mode, ultrasonic transducer
114 airflow sensor
116 patient event switch
118 electronic stethoscope
120 temperature probe
122 user adjustable gain controls
124 status display
126 user marker switch
128 power switch
200 ECG/EEG/Muscle signal conditioning and switching circuitry
202 airflow pressure transducer circuitry
204 ultrasound generator and transducer circuitry
206 finger pulse oximeter LED drive and photodiode circuitry
208 temperature probe transducer circuitry
210 audio switching and power amplifiers circuitry
212 stethoscope microphone amplifier and filter circuitry
214 high voltage pulse generator circuitry
216 status display circuitry
218 Electrically Erasable Programmable Read Only Memory (EEPROM) for host interface and display microcontroller
220 Sixteen channel analog mulitplexer and analog-to-digital converter
222 general digital input/output and status sense circuitry
224 status signals from peripheral circuitry
226 control signals to peripheral circuitry
228 digital-to-analog converter
230 voltage controlled oscillator
232 host interface and display microcontroller
234 data, address, and control busses of host interface and display microcontroller
236 dual port static Random Access Memory (RAM)
238 digital signal processor
240 power supplies circuitry
242 interface transceivers circuitry
244 external printer interface
246 Electrically Erasable Programmable Read Only Memory (EEPROM) for digital signal processor
248 battery status and charge control circuitry
250 rechargeable battery
252 data, address, and control busses of digital signal processor
254 external printer
256 external battery charger
258 parallel printer port interface

DESCRIPTION OF INVENTION

A typical embodiment of the physiological monitoring system described in this patent is illustrated in FIG. 1. The principal physical components of this system are the set of attached sensors and auxiliary devices, an electronics unit 100, and a portable personal computer 102. Additional support components include an external printer 254 and battery charger 256 (shown in the systems diagram of FIG. 2).

Figure 2:
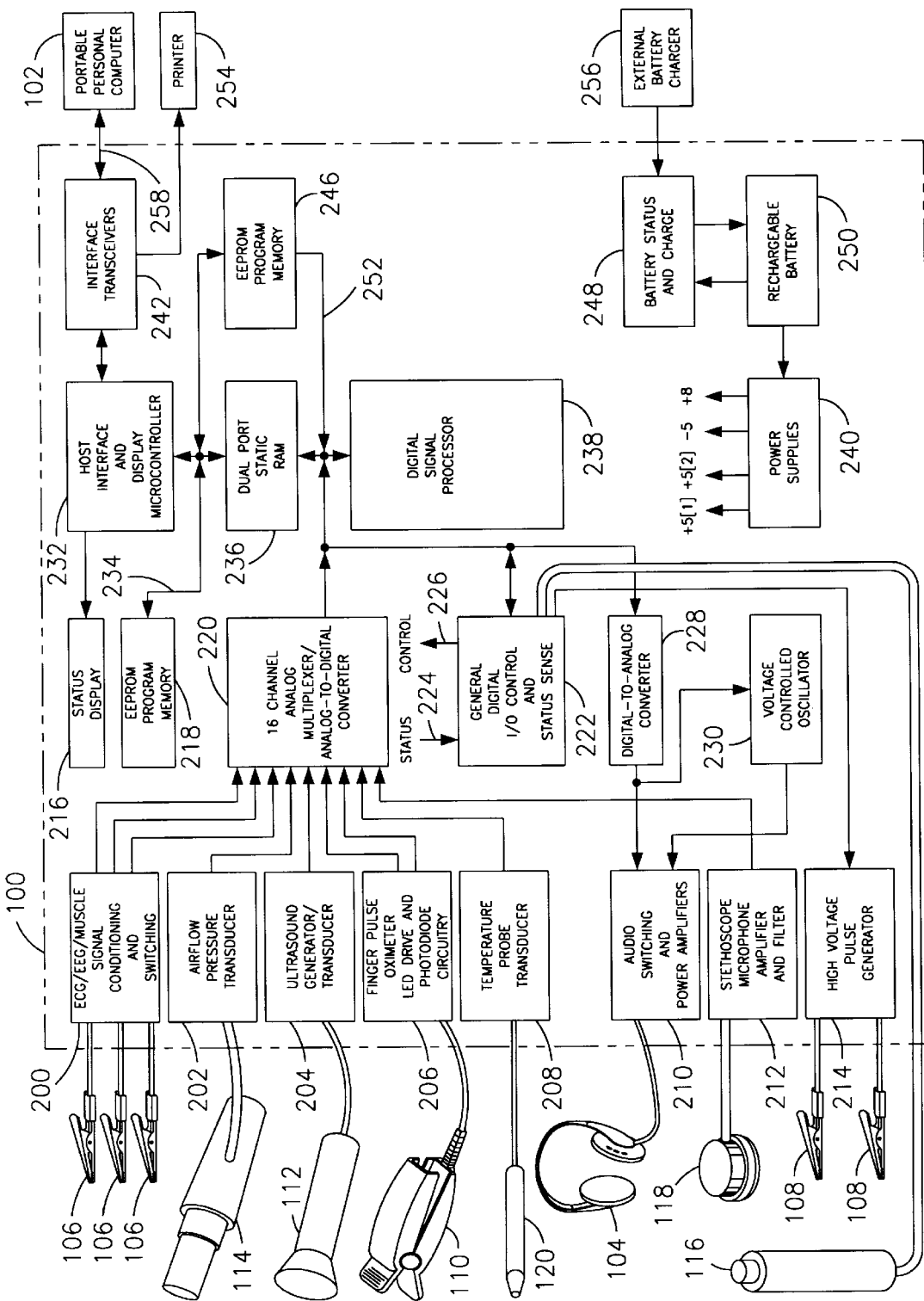
FIG. 2 shows a systems view of the electronics unit with attached sensors, portable personal computer, external printer and external battery charger.

Electronics unit 100 of the system consists of an enclosure that contains circuitry to support the acquisition and processing of signals obtained from the sensors. The front panel of this electronics unit contains user adjustable gain controls 122 used by the internal circuitry to set user adjusted gains. A status display 124 on the front panel will assist the user in assessing the unit's status however, the display of portable personal computer 102, will be the principal display used in status reporting. A user marker switch 126 allows direct interaction with electronics unit 100 during some operations. A power switch 128 enables/disables power to the electronics unit. Various sensors and auxiliary devices attached to the side and back panel of electronics unit 100. Portable personal computer 102 can be placed on top of electronics unit 100 for space savings or can be located adjacent to the unit. FIG. 2 also shows a parallel printer port interface 258 which allows for communication between electronics unit 100 and portable personal computer 102. An external printer 254 attaches to electronics unit 100 at its rear panel.

A plethora of sensors and auxiliary devices attach to electronics unit 100 as shown in FIGS. 1 and 2. A pair of stereo headphones 104 allow the human subject to be presented various audio waveforms generated by electronics unit 100. Alligator clips 106 consist of ten miniature alligator clips that attach to a human subject via disposable tab electrodes. FIGS. 1 and 2 show only three of these clips for illustrative purposes however, ten of them are required for acquisition of a 12-lead electrocardiogram. These clips can also be used for acquisition of electroencephalographic and neuromuscular signals from a human subject. Alligator clips 108 consist of two miniature alligator clips that attach to a human subject via disposable tab electrodes. These clips apply high voltage pulses to the human subject for stimulation associated with nerve conduction studies. A finger pulse oximeter 110 is a standard oximeter that can be attached to a human subject's finger for acquisition of blood oxygen saturation signals via standard photometric techniques. An ultrasonic transducer 112 transmits and receives M-mode ultrasound to a human subject. An airflow sensor 114 enables measurement of airflow from a human subject during pulmonary function testing. A patient event switch 116 allows a human subject to interact with electronics unit 100 and indirectly with portable personal computer 102. An electronic stethoscope 118 enables auscultation of heart and lung sounds from a human subject and allows for acquisition and recording of these sounds via electronics unit 100. A temperature probe 120 enables temperature measurements of the human subject. Other sensors capable of physiological monitoring could be interfaced with electronics unit 100 but are not shown in this embodiment. These could include devices such as noninvasive blood pressure monitors.

FIG. 2 shows a systems diagram of the physiological monitoring system of this patent. Electrocardiographic, electroencephalographic and neuromuscular signals arrive at ECG/EEG/Muscle signal conditioning and switching circuitry 200 where they are amplified by gains set by either front panel user adjustable gain controls 122 or by commands sent from portable personal computer 102. This circuitry also has preliminary signal filters for the arriving signals. The output of this circuitry consists of three separate analog signals which are presented to sixteen channel analog multiplexer and analog-to-digital converter 220 for conversion to digital signals. Groups of three signals are selected by control signals 226 arising from general digital input/output control and status sense circuitry 222 for the purpose of routing standard sets of electrocardiographic signals to sixteen channel analog multiplexer and analog-to-digital converter 220 for conversion to digital signals.

Pressure waveforms from airflow sensor 114 are applied to the pressure transducer within airflow pressure transducer circuitry 202. The analog pressure signal from this circuitry is a function of the rate of airflow delivered to airflow sensor 114 from the human subject. After filtering the signal from this circuitry, the analog signal is presented to sixteen channel analog multiplexer and analog-to-digital converter 220 for conversion to digital signals.

M-mode, ultrasonic transducer 112 has its ultrasonic generator supplied by energy from ultrasound generator and transducer circuitry 204 which in turn is controlled by control signals 226 arising from general digital input/output control and status sense circuitry 222. Reflected energy from the tissues in the human subject is transduced by M-mode, ultrasonic transducer 112 and the signal from this device is amplified and filtered by ultrasound generator and transducer circuitry 204. The analog signal from this circuitry is presented to sixteen channel analog multiplexer and analog-to-digital converter 220 for conversion to digital signals.

Finger pulse oximeter 110 has its infrared and red light emitting diodes driven by finger pulse oximeter LED drive and photodiode circuitry 206 which in turn is controlled by control signals 226 arising from general digital input/output control and status sense circuitry 222. Transmitted light waveforms from finger pulse oximeter's 110 photodiode are amplified and filtered by finger pulse oximeter LED drive and photodiode circuitry 206 and the two analog signals from this circuitry are presented to sixteen channel analog multiplexer and analog-to-digital converter 220 for conversion to digital signals. Amplification of the light waveforms is selectively controlled by control signals 226 arising from general digital input/output control and status sense circuitry 222.

The analog signal from temperature probe 120 is amplified and filtered by temperature probe transducer circuitry 208 and this signal is presented to sixteen channel analog multiplexer and analog-to-digital converter 220 for conversion to digital signals.

Stereo auditory signals are generated by audio switching and power amplifiers circuitry 210 and presented to stereo headphones 104 worn by the human subject. The source of these auditory signals can be from digital-to-analog converter 228 or from voltage controlled oscillator 230 whose frequency is controlled by the voltage output from digital-to-analog converter 228. Voltage controlled oscillator 230 allows for simpler and purer generation of auditory test tones during audiometric testing of the human subject. Volume levels supplied to stereo headphones 104 can be controlled by either front panel user adjustable gain controls 122 or by digital control from digital signal processor 238 (pathway not explicitly shown in FIG. 2 for drawing clarity purposes) via a digital-to-analog converter within audio switching and power amplifiers circuitry 210.

The analog signal from electronic stethoscope 118 is amplified and filtered by stethoscope microphone amplifier and filter circuitry 212 prior to it being sent to sixteen channel analog multiplexer and analog-to-digital converter 220 for conversion to digital signals. The gain of the amplifier can be controlled from front panel user adjustable gain controls 122.

High voltage pulse generator circuitry 214 generates 70 Volt, 50 to 500 microsecond pulses to alligator clips 108 for use in nerve conduction studies as well as for use in Transcutaneous Electrical Nerve Stimulation (TENS) therapy. Control of these pulses occurs from control signals 226 derived from general digital input/output control and status sense circuitry 222.

Patient event switch 116 routes human subject responses to general digital input/output control and status sense circuitry 222.

Digital signal processor 238 executes control instructions from Electrically Erasable Programmable Read Only Memory (EEPROM) 246 and is the principal component effecting retrieval, preprocessing, and transmission of sensor data to portable personal computer 102 via host interface and display microcontroller 232. Control instructions, information, and general control of digital signal processor 238 occur via signals from data, address, and control busses of the digital signal processor 252. This processor has access to the digital words that are generated from sixteen channel analog multiplexer and analog-to-digital converter 220. It also exerts general control over most of the circuitry in electronics unit 100 via general digital input/output control and status sense circuitry 222 through control signals 226. Status signals 224 from the circuitry within electronics unit 100 are sensed by general digital input/output control and status sense circuitry 222 and are interrogated by digital signal processor 238. Command and status semaphores from host interface and display microcontroller 232 are communicated to digital signal processor 238 via dual port static Random Access Memory (RAM) 236 and temporary data to and from digital signal processor 238 is also communicated through this RAM. Electrically Erasable and Programmable Read Only Memory (EEPROM) 246 used by digital signal processor 238 for storage of control instructions, is also modifiable by host interface and display microcontroller 232. Digital signal processor 238 is able to send data words to digital-to-analog converter 228 as well as the digital-to-analog converter located in the audio switching and power amplifiers circuitry 210.

Host interface and display microcontroller 232 executes control instructions from Electrically Erasable and Programmable Read Only Memory (EEPROM) 218 and is principally responsible for receiving commands from portable personal computer 102 and communicating these commands to digital signal processor 238 via dual port static Random Access Memory (RAM) 236. This processor also is responsible for communicating information generated by digital signal processor 238 to portable personal computer 102 and vice versa. Control instructions, information, and general control of host interface and display microcontroller 232 occur via signals from data, address, and control busses of the host interface and display microcontroller 234. Host interface and display microcontroller 232 interfaces to parallel printer port interface 258 of portable personal computer 102 via interface transceivers circuitry 242. Interface transceivers circuitry 242 has the capability of routing information to/from host interface and display microcontroller 232 to portable personal computer 102, or can route information from portable personal computer 102 to external printer 254 via external printer interface 244 when printing is required by portable personal computer 102. Host interface and display microcontroller 232 can execute control instructions from Electrically Erasable Programmable Read Only Memory (EEPROM) 246 that is normally used by digital signal processor 238 when it is necessary to reconfigure its own control instructions that are normally located in Electrically Erasable Programmable Read Only Memory (EEPROM) 218. This microcontroller also controls status display circuitry 216 for the status display 124 on the front panel of electronics unit 100 to allow display of system status independent of portable personal computer 102.

A rechargeable battery 250 provides the power for electronics unit 100 via power supplies circuitry 240. This battery's charging control and status is monitored by a battery status and charge circuitry 248. An external battery charger 256 provides power to battery status and charge circuitry 248 for the purpose of charging rechargeable battery 250 as well as providing power to electronic unit 100 when commercial power is available. Power supplies circuitry 240 generates the necessary voltages required by electronics unit 100.

Operation of Invention

Four principal modes of operation can be invoked with this physiological monitoring system. Each of these modes will be described in detail below. It is the ability of the system to perform the third mode of operation that makes this system unique secondary to its architecture of objects and advantages stemming from this architecture.

The first mode of operation is the mode of monitoring a single physiological parameter from a human subject and displaying either a static value obtained, or continuously displaying values realtime. This mode is useful in monitoring temperature, electrocardiographic waveforms, electroencephalographic waveforms, neuromuscular waveforms, phonocardiographic waveforms, phonopulmonary waveforms, finger pulse oximetry, and adipose tissue measurements.

An example of the first mode of operation will be illustrated for the measurement of temperature from a human subject. The user in this case (i.e. the clinician) will attach temperature probe 120 to the human subject in the area of interest. The user will invoke the continuous temperature monitoring mode from the application program that is executing on portable personal computer 102. This program will communicate with electronics unit 100 via parallel printer port interface 258 and send electronics unit 100 a command that will instruct the unit to begin making temperature measurements from temperature probe 120. The command will be interpreted initially by host interface and display microcontroller 232 which will subsequently task digital signal processor 238 to initiate temperature measurements from temperature probe 120 via temperature probe transducer circuitry 208. Digital signal processor 238 will acquisition digital words from sixteen channel analog multiplexer and analog-to-digital converter 220 and hold these words within dual port static Random Access Memory (RAM) 236. As these words fill this memory, host interface and display microcontroller 232 transmits these words back to portable personal computer 102 via parallel printer port interface 258 where the application program receives and displays these words in an appropriate format for the user. The user would be allowed to use various different modes of acquisition of temperature as allowed by the application program. For example, the rate of temperature sampling could be quite variable from one sample an hour to many thousands of samples per second. The capability of logging temperature samples to the hard disk drive of portable personal computer 102 could be another mode of the application program. In this example, one can easily see that portable personal computer 102 can allow for many different modes of capability of the entire physiological monitoring system via its ability to be programmed to fulfill these modes and without having to change the hardware of any part of the system. Portable personal computer 102 also allows for a multitude of display, storage, and user interaction options through its programmable features. Information gathered in a session such as this one involving temperature monitoring, could be integrated into the subject's database of medical information by having the application program interact with the database application via file systems.

A second mode of operation of this physiological monitoring system involves the acquisition of physiological parameters from a human subject whereby the subject and/or the user must physically interact with the system in order for the system to be able to acquisition the desired physiological parameter. Examples of this mode of operation are pulmonary function testing, audiological testing, nerve conduction studies, reaction time testing, memory sequence testing, ultrasonic measurements, and biofeedback sessions. In each of these examples, one physiological parameter is being measured by the system but, its measurement is dependent on the interaction with the human subject and/or user at specific time intervals during the testing.

An example of the second mode of operation will be illustrated using pulmonary function testing. The user in this case will utilize airflow sensor 114 to measure airflow rates and air volumes that are routinely measured in most pulmonary function tests. The user invokes the pulmonary function test mode from the application program that is executing on portable personal computer 102. Unlike the previous mode described, this mode of testing must coordinate the testing with the user/human subject by signaling him/her from the display of personal portable computer 102 to begin taking a deep inspiration and then subsequently expiring as hard and quickly as he/she can. During this time, portable personal computer 102 will begin sending commands via parallel printer port interface 258 to electronics unit 100 in a similar fashion to that described in the above temperature monitoring example. The difference here is that the application program will send sequential commands to electronics unit 100 in realtime, acquisitioning the airflow rates from airflow sensor 114 as the subject sequences through the steps of inspiration and expiration. Upon completion of the steps, the application program will calculate spirometric volumes based on the airflow information that it received during the test and generate test results on the display of portable personal computer 102 in the form of tables and graphs. This information can in turn, be integrated into the patient's database on the hard disk drive of portable personal computer 102.

A third mode of operation of this physiological monitoring system involves the simultaneous acquisition of multiple physiological parameters with or without interaction between the user and/or human subject. Examples of this mode of operation are multiple sleep latency measurements that involve monitoring of electrocardiographic, electroencephalographic, and oxygen saturation parameters on a continuous basis as well as biological age measurements. A similar scheme to the two previous modes is used by the application program executing on portable personal computer 102 in issuing commands to electronics unit 100 and receiving sensor information from this unit.

The fourth mode of operation of this physiological monitoring system involves the transmission of commands from the application program executing on portable personal computer 102 to electronics unit 100 without feedback of any information back to the application program. An example of this mode is in the generation of pulses used in Transcutaneous Electrical Nerve Stimulation (TENS) therapy. In this example, pulse width commands are sent to electronics unit 100 similar to commands of the previously described modes to generate high voltage pulses in high voltage pulse generator circuitry 214. These pulses are applied to the human subject but no physiological monitoring of any parameter is acquisitioned from the subject in this application.

Auxiliary, lower level operations of electronics unit 100 include the generation of status to status display 124 via status display circuitry 216 and, internal power generation from rechargeable battery 250 via power supplies circuitry 240, as well as charge control of rechargeable battery 250 via battery status and charge circuitry 248 and external battery charger 256. I will defer discussion of these subsystems of the electronics unit in this document as they do not impact on the novelty of operation of the overall physiological monitoring system and their theory of operation is easily deduced by the average layperson in this field.

SUMMARY, RAMIFICATIONS, AND SCOPE

Accordingly, the reader should be convinced from the above description and operations sections that the physiological monitoring system presented here is unique in its ability to perform many useful physiological monitoring tasks within a clinical outpatient environment in a manner that is cost effective in the components and their architecture that comprise this system. The versatility that is provided by its architecture in the various modes of operation that it can perform will offer many clinical outpatient environments capabilities that were not attainable prior to the conception of this system. Furthermore, this physiological monitoring system has additional advantages in that it permits the system to not only be used portably within the clinical outpatient environment, but can have utility in remote environments such as nursing homes, residences, auxiliary offices, harsh environments such as battlefields, public gatherings, and mobile situations;

its architecture permits the easy addition of future devices to the electronics to allow for more parameter measurement capabilities without having to alter the overall architecture of the system;

its architecture also permits multiple combinations of physiological parameter gathering scenarios that may not yet be defined in current methods of disease diagnoses and monitoring;

it permits for future change of the portable personal computer to other computing/control elements since the functions of parameter gathering via the electronics are separated from the application program executing on the computing/control element;

it permits for an excellent bridge between office information systems in the clinical outpatient environment and more centralized systems that are continuing to evolve in the healthcare system.

Although the description above contains many specifications, these should not be construed as limiting the scope of the invention but as merely providing illustrations of some of the presently preferred embodiments of this invention. For example, although the interface between electronics unit 100 and portable personal computer 102 has been designated here as a parallel printer port interface, other interfaces such as an infrared interface or a high-speed serial interface would work equally well in this situation. These interfaces were not chosen for the preferred embodiment of this invention only because they are not as available on current versions of most portable personal computers. Also, there is no reason to believe that other computing elements besides the portable personal computer used in the preferred embodiment of this invention, can't be substituted for the portable personal computer used here. A desktop or palm computer could be used as the computing element instead of the portable personal computer. Finally, it should not be construed that this physiological monitoring system be used only in an clinical outpatient environment. It could have equal or greater utility in other environments also.

Thus the scope of the invention should be determined by the appended claims and their legal equivalents, rather than by the examples given.

I claim:

1. A portable, physiological monitoring system configured to monitor physiological parameters of a human subject, the system comprising:

a) a portable personal computer including an applications program executable thereon to produce a command, and having a display, a user input, and a data storage configured to contain existing information related to the human subject;

b) at least one physiological sensor, configured to be attached to the human subject to sense a physiological parameter of the human subject and to produce a signal representing the physiological parameter; and c) a portable electronics unit, separate from the portable personal computer, the at least one physiological sensor and the human subject, and having circuitry connected to the at least one physiological sensor and the portable personal computer, the circuitry being responsive to the command from the applications program to initiate acquisition of the signal from the at least one sensor, the circuitry being configured to manipulate the signal and send the signal to the portable personal computer; and d) the portable personal computer being configured to display the physiological parameter on the display, and to store the physiological parameter in the data storage with the existing information related to the human subject.

2. The system of claim 1, wherein the portable personal computer is continuously connected to the electronics unit during operation; wherein the portable personal computer is configured to control the electronics unit in real-time; and wherein the portable personal computer is configured to display the physiological parameter on the display in real-time.

3. The system of claim 1, wherein the portable personal computer is removably disposed on top of the electronics unit to save space.

4. The system of claim 1, wherein the at least one physiological sensor includes multiple physiological sensors configured to sense multiple physiological parameters; and wherein the circuitry of the electronics unit includes conversion and manipulation circuitry common to the multiple physiological sensors.

5. The system of claim 1, wherein the electronics unit includes:
   a) a user adjustable gain control, connected to the circuitry, configured to allow a user to adjust gain;
   b) a user marker switch, connected to the circuitry, configured to allow the user direct interaction with the electronics unit; and
   c) a status display, connected to the circuitry, configured to display the status of the electronics unit.

6. The system of claim 1, wherein the portable personal computer, portable electronics unit, and at least one physiological sensor have at least three modes of operation, including:
   a) a first mode of operation in which the at least one physiological sensor is configured to sense a single physiological parameter, and the display of the portable personal computer is configured to display the parameter as either a static value or as continuous, real-time values;
   b) a second mode of operation in which the at least one physiological sensor is configured to sense a physiological parameter in conjunction with interaction by the human subject, and the portable personal computer is configured to signal the human subject to perform an act in conjunction with the physiological parameter; and
   c) a third mode of operation in which the at least one physiological sensor includes multiple physiological sensors configured to simultaneously sense multiple physiological parameters.

7. The system of claim 1, wherein the electronics unit is configured to generate electrical pulses which are applied to the human subject.

8. The system of claim 1, wherein the portable personal computer further has a parallel printer port; wherein the electronics unit and portable personal computer connect through the parallel printer port; further comprising an external printer connected to the electronics unit; and wherein the portable personal computer is configured to print information by sending the information through the parallel printer port, through the electronics unit, to the printer.

9. A portable, human subject, physiological monitoring system for clinical outpatient environments, the system comprising:
   a) at least one physiological sensor configured to be attached to the human subject, sense a physiological parameter of the human subject, and produce a signal representing the physiological parameter;
   b) a portable electronics unit, coupled to the at least one sensor and configured to be separate from the human subject, and having circuitry connected to the at least one sensor to acquire and process the signal from the at least one sensor; and
   c) a portable personal computer, separate from and coupled to the electronics unit, to control the electronics unit in real-time and to receive information from the electronics unit, the portable personal computer having an application program executable thereon to produce a command to send to the electronics unit to initiate acquisition of the signal from the at least one sensor, and having:
      i) a display configured to display the information from the electronics unit;
      ii) an interface configured to receive user input; and
      iii) a data storage configured to contain existing information related to the human subject and to store information acquired such that existing and new information are integrated.

10. The system of claim 9, wherein the portable personal computer is removably disposed on top of the electronics unit to save space.

11. The system of claim 9, wherein the at least one physiological sensor includes multiple physiological sensors configured to sense multiple physiological parameters; and wherein the circuitry of the electronics unit includes conversion and manipulation circuitry common to the multiple physiological sensors.

12. The system of claim 9, wherein the circuitry of the electronics unit is configured to perform lower level operations, and the portable personal computer is configured to perform higher level operations.

13. The system of claim 9, wherein the electronics unit includes:
   a) a user adjustable gain control, connected to the circuitry, configured to allow a user to adjust gain;
   b) a user marker switch, connected to the circuitry, configured to allow the user direct interaction with the electronics unit; and
   c) a status display, connected to the circuitry, configured to display the status of the electronics unit.

14. The system of claim 9, wherein the portable personal computer, portable electronics unit, and at least one physiological sensor have at least four modes of operation, including:
   a) a first mode of operation in which the at least one physiological sensor is configured to sense a single physiological parameter, and the display of the portable personal computer is configured to display the parameter as either a static value or as continuous, real-time values;
   b) a second mode of operation in which the at least one physiological sensor is configured to sense a physiological parameter in conjunction with interaction by the human subject, and the portable personal computer is configured to signal the human subject through the display to perform an act in conjunction with the physiological parameter;
   c) a third mode of operation in which the at least one physiological sensor includes multiple physiological sensors configured to simultaneously sense multiple physiological parameters; and
   d) a fourth mode of operation in which the electronics unit is configured to generate electrical pulses which are applied to the human subject.

15. A method for obtaining, displaying and integrating human subject physiological information from a human subject, comprising the steps of:

a) attaching a physiological sensor to the human subject;

b) disposing a portable electronics unit adjacent the human subject, but separate from the human subject, and connecting the physiological sensor to the portable electronics unit;

c) connecting a portable personal computer to the electronics unit;

d) operating an application program executable on the portable personal computer to send a command to the electronics unit to initiate acquisition of the physiological parameter;

e) sensing the physiological parameter and producing a signal using the physiological sensor;

f) manipulating the signal using the electronics unit;

g) communicating the sensed parameter to the portable personal computer; and h) displaying the parameter on a display of the portable personal computer; and storing the parameter in the data storage of the portable personal computer.

16. The method of claim 15, further comprising accessing existing information with respect to the human subject contained in the data storage of the portable personal computer.

17. The method of claim 15, further comprising removably disposing the portable personal computer on top of the electronics unit to save space.

18. The method of claim 15, further comprising:

a) sensing multiple physiological parameters and producing multiple signals using multiple physiological sensors; and b) manipulating the signals using common circuitry of the electronics unit.

19. The method of claim 15, further comprising a) manually adjusting the gain using a user adjustable gain control of the electronics unit;

b) directly interacting with the electronics unit using a user marker switch; and c) displaying the status of the electronics unit using a status display of the electronics unit.

20. The method of claim 15, further comprising selectively operating the portable personal computer, electronics unit, and sensor in at least four modes of operation, including:

a) a first mode of operation by sensing a single physiological parameter with the physiological sensor, and displaying the parameter as either a static value or as continuous, real-time values using a display of the portable personal computer;

b) a second mode of operation by sensing a physiological parameter using the physiological sensor in conjunction with interaction by the human subject, and prompting the human subject to perform an act using the display of the portable personal computer;

c) a third mode of operation by simultaneously sensing multiple physiological parameters using multiple physiological sensors; and d) a fourth mode of operation by generating electrical pulses using the electronics unit and applying the electrical pulses to the human subject.

* * * * *